United States Patent [19]
Spitler

[11] Patent Number: 5,738,867
[45] Date of Patent: Apr. 14, 1998

[54] ANTITUMOR VACCINES

[75] Inventor: Lynn E. Spitler, Tiburon, Calif.

[73] Assignee: Jenner Technologies, Tiburon, Calif.

[21] Appl. No.: 469,309

[22] Filed: Jun. 6, 1995

Related U.S. Application Data

[63] Continuation of Ser. No. 151,568, Nov. 12, 1993, abandoned, which is a continuation of Ser. No. 800,474, Nov. 26, 1991, abandoned.

[51] Int. Cl.$^6$ ............................................. A61K 9/127
[52] U.S. Cl. ............................................ 424/450; 436/829
[58] Field of Search ................................ 424/450; 436/829

[56] References Cited

U.S. PATENT DOCUMENTS

| | | | |
|---|---|---|---|
| 4,343,895 | 8/1982 | Sugaar | 435/172.2 |
| 4,557,931 | 12/1985 | Irie et al. | 424/88 |
| 5,026,557 | 6/1991 | Estis et al. | 424/450 |
| 5,141,742 | 8/1992 | Brown et al. | 424/88 |

FOREIGN PATENT DOCUMENTS

| | | |
|---|---|---|
| 0036277 | 9/1981 | European Pat. Off. . |
| 2188532 | 7/1990 | Japan . |

OTHER PUBLICATIONS

Philips et al., Cancer det. & Prev. 14, #4, p. 1990, 1990.
Heath et al., Methods in Enzymology 1987 149, p.111.
Sela et al., Hybridoma 8, #4, 1989, p. 481.
Szala et al., PNAs 87, p. 3542, 1990.
DATABASE WPI–Week 9035 –Derwent Publications Ltd. London GB AN 90–266194 & JP 02 188 532 A (Otsuka Pharm Co Ltd) 24 Jul. 2990 –Abstract.
J. Gen Virol. vol 65, 1984, London (GB), pp. 1009–1014, XP002036804 A.R. Neurath et al. "Antibodies to hepatitis B surface antigen (HBsAg) elicited by immunization with a synthetic peptide covalently linked to liposomes"–whole document.
Sela et al., "Colon Carcinoma–Associated Glycoproteins Recognized by Monoclonal Antibodies Co–029 and GA22–2", Hybridoma 8(4):481–491 (1989).
Szala et al., "Molecular cloning of cDNA for the carcinoma–associated antigen GA733–2", Proc. Natl. Acad. Sci. USA 87:3542–3546 (1990).

*Primary Examiner*—Gollamudi S. Kishore
*Attorney, Agent, or Firm*—Morrison & Foerster LLP

[57] ABSTRACT

Antitumor vaccine compositions and methods for treating tumors that express the GA733-2 antigen are disclosed. The vaccines comprise a GS733-2 antigen in a liposomal carrier.

6 Claims, No Drawings

ANTITUMOR VACCINES

This application is a continuation of application Ser. No. 08/151,568 filed 12 Nov. 1993 now abandoned, which is a continuation of application Ser. No. 07/500,474, filed Nov. 26, 1991, which is abandoned.

BACKGROUND OF THE INVENTION

1. Field of the Invention

The present invention relates to the field of cancer therapy, and particularly the treatment and prevention of cancer with anti-cancer vaccines comprising tumor associated antigens encapsulated in or conjugated to liposomes.

Cancer is the second leading cause of death in the United States accounting for almost 500,000 deaths each year. More than 1,000,000 new cases of cancer are diagnosed in the United States annually. The incident of cancer is increasing largely as a byproduct of the greater lifespan of the aging population. Cancer is a leading cause of death in all industrialized nations, where life expectancy continues to increase. It is expected that cancer morbidity and mortality will continue to increase in all industrialized areas of the world.

Cancer of the lung is the most common malignancy in the U.S. Neoplasms of the lung and gastrointestional tract account for 30% of all malignancies. There are over 160,000 new cases of lung cancer annually in the U.S. with 143,000 annual fatalities. Seventy percent of lung cancer patients die of recurrent tumor following "curative" surgery. The five year survival following diagnosis is 10%.

Colorectal cancer is currently the second most commonly occurring cancer in the United States. The present incidence of colorectal cancer in the U.S. is about 150,000 cases new cases per year with a mortality approaching 60,000 per year. The five year survival following diagnosis is 50%.

Melanoma strikes about 32,000 patients per year in the U.S. The incidence of melanoma is dramatically increasing and by the year 2000, 1 of every 100 Americans will develop melanoma at some point in their lifetime.

Other forms of cancer, including ovarian, pancreatic, and especially breast continue to be major causes of cancer related mortality.

Almost all forms of cancer continue to be refractory to treatment despite many years of therapeutic experience. Vaccine development has been slow and no vaccine currently exists for any form of cancer. There is, therefore, a continuing need for the development of new therapeutic and prophylactic compounds efficacious in the prevention and treatment of all forms of cancer.

2. Description of the Relevant Literature

U.S. Pat. No. 4,343,895 discloses methods for the detection of cancer with tumor-specific antigens encapsulated in liposomes. The disclosures are limited to the use of such compounds in an ex-vivo technique for detecting cancer cells.

U.S. Pat. Nos.: 4,891,208 and 4,721,612 disclose the use of liposomes as adjuvants.

U.S. Ser. No. 07/575,567 describes DNA and polypeptide for tumor-associated antigen CO-029 and describes the coupling of the polypeptide compounds with larger moieties in order to enhance the immunogenicity of the polypeptide compounds for use as a cancer vaccine.

U.S. Ser. No. 07/291,583 describes DNA and polypeptide for tumor-associated antigen GA 733-1 and GA 733-2 and describes the use of antibody compounds to the antigen for use as a cancer vaccine.

JP 2188532 describes tumor surface antigen protein reconstituted into liposomes containing 1,2-dimyristoylamido - 1,2-deoxyphosphatidylcholine.

Heath, T. D., *Methods Enzymol.* (1987)149:111–19, describes the covalent attachment of proteins to liposomes.

Phillips, N. C., et al., *Cancer Det. & Prev.* (1990) 14:491–496, describe a clinical trial of a liposomal tumor antigen associated with human melanoma and claims efficacy of the experimental compounds.

All references cited are incorporated herein by reference.

SUMMARY OF THE INVENTION

The present invention comprises methods and compositions employing liposome compositions encapsulating or conjugated to tumor associated antigens (TAAs) or anti-idiotypic monoclonal antibodies to TAAs. The compositions are useful as vaccine-like compounds for the prevention and treatment of a variety of cancers. Of particular interest are liposome compositions encapsulating the TAAs CO-029, associated with tumors of the gastrointestinal tract, colorectum, and pancreas and GA733-2, associated with tumors of the gastrointestinal tract, prostate, cervix, ovary, bladder, lung, breast, colorectum, and pancreas. In an alternate embodiment, TAAs are conjugated to liposomes.

DETAILED DESCRIPTION OF THE INVENTION

According to the subject invention, liposomes are generally produced from phospholipids or other lipid substances. They can have one bilayer (unilamellar) or two or more bilayers (multilamellar). Liposomes containing pure tumor associated antigens (created by genetic engineering, hybridoma technology (monoclonal antibodies), or synthesized) are useful in targeting therapeutic agents to the reticuloendothelial system, one of the sites of generation of the immune response in a mammalian host, including humans.

Procedures for the preparation of liposomes are well known to those of skill in the art and do not fall within the scope of the present invention. Any lipid capable of forming vesicles can be employed. For clinical application, it is desirable that the lipid be non-toxic, physiologically acceptable, and metabolizable. Common bilayer forming lipids having clinical potential are phospholipids, fatty acids, sphingolipids, glycosphingolipids, and steroids. Glycerol containing phospholipids are the most commonly used component of liposome formulations having clinical utility. One commonly used example is phosphatidylcholine or lecithin. The steroid cholesterol and its derivatives are often included as components of liposomal membranes. The tendency of liposomes to aggregate and fuse can be controlled by the inclusion of small amounts of acidic or basic lipids in the formulation. The properties of liposomes containing phospholipids are determined by the chemistry of the phospholipid. Important considerations are the hydrocarbon chain length, degree of unsaturation of the hydrocarbon chain, degree of branching of the hydrocarbon chain, and temperature of the system.

Techniques and apparatus known to those skilled in the art can be employed to form liposomes according to the subject invention. Multilamellar liposomes can be created by depositing a mixture of lipids as a thin film by evaporation under reduced pressure followed by dispersion with an excess volume of aqueous buffer containing the antigen with or without organic solvents. Another method is to mix the aqueous phase containing the antigen with small unilamellar liposomes followed by lyophilization. The multilamellar liposomes are formed when the lyophilized product is rehydrated, usually with a small amount of distilled water. The small unilamellar liposomes to be used in this process are produced by dispersing the lipids in an aqueous medium followed by a mechanical means of dispersion such as sonication, use of a high pressure device, or a solvent injection method. Large and intermediate sized unilamellar liposomes can also be produced by conventional techniques including detergent dialysis, extrusion through small pore size membranes under high pressure, freeze thawing followed by slow swelling, dehydration followed by rehydration and dilution, or dialysis of lipids in the presence of chaotropic ions. The size of the liposomes can be made more uniform by fractionation procedures such as centrifugation or size exclusion chromatography, homogenization, or capillary pore membrane extrusion.

The target within the host and major site of uptake of liposomes is the reticuloendothelial system, mainly in the liver, spleen, and lung of the host. Factors affecting uptake of liposomes by the host include liposome size, stability and surface charge. The apparent optimal size for targeting the reticuloendothelial system is >1.0 µm, particularly for targeting liver, lung, and spleen.

According to the subject invention, antitumor vaccine compositions are formed by encapsulating tumor associated antigens or TAAs with intermediate sized liposomes. Water soluble TAAs, which may partition into either the lipid bilayer or the aqueous component, are added to the aqueous phase before formation of liposomes in order to entrap the agent with the liposomes during formation. Alternatively, lipid soluble TAAs are added to the lipid mixture before formation of the liposomes wherein the TAA partitions into the lipid bilayer. Lipophilic TAAs may require detergent dialysis.

In an alternate embodiment of the invention, TAAs of interest are conjugated to the surface of liposomes by techniques known to those of skill in the an. Of particular interest is the conjugation of the TAAs CO-029 or GA733-2, or anti-idiotypic monoclonal antibodies to these TAAs, by covalent attachment. It is believed that the conjugation of TAAs to liposomes provides a different presentation of the antigen within the host, illiciting a different immune response than that achieved with encapsulated forms of TAA-liposome compositions. Methods for conjugation employ glutaraldehyde, diethylsuberimidate, or other homobifunctional reagents. Torchilin et al., *Biochem. Biophysics. Res Commun.* (1978)85:983. Preferred methods of conjugation employ efficient, selective reactions in aqueous media. For example, carboxyl groups activated with N-hydroxysuccinimide may be reacted with amino groups to produce an amide, or pyridyldithiols are reacted with thiols to produce disulfide bonds, or maleimide derivatives are reacted with thiols to produce thioether bonds. Any of these three techniques may be employed with nearly equal utility to form TAA-liposome conjugates as described below. Alternatively, the proteins may be directly coupled to derivatized lipid molecules and subsequently inserted into preformed liposomes.

Procedures for the production of pure TAAs are well known to those skilled in the art. Currently there are four general categories of methods for the production of TAAs:

1) Production of the cDNA done of the desired TAA and expression in a suitable vector;

2) Production of anti-idiotypic antibodies bearing the internal image of the desired TAA through hybridoma technology;

3) Purification of the desired antigen from a source unrelated to the tumor; and, 4) Synthesis of the desired antigen.

Examples of TAAs for which the cDNA has been identified and cloned include TAA of lung and colon carcinoma termed CO 17-1A or KS¼, carcinoembryonic antigen, and a melanoma associated antigen. These genes, as well as other TAA genes, are expressed in a suitable recombinant expression vector such as recombinant baculovirus and the resulting recombinant baculovirus then used to infect susceptible cultured SF9 cells (*Spodoptera frugiperda* insect cells) to produce the protein product of the gene as described in U.S. Pat. No. : 4,879,236.

Examples of TAAs so produced include those for melanoma as described by Kahn et al., *Cancer Res.* (1989) 49:3157–62 and Kusama et al., *J. Immunol.* (1989) 143:3844–52 and carcinoembryonic antigen as described by Vialo et al., *J. Immunol.* (1987)139:4250. Such anti-ids are produced from hybridoma cells in tissue culture and incorporated into liposomes according to the subject invention.

Alternatively, antigens which mimic the desired TAAs are produced by creating anti-idiotypic antibodies or anti-ids (Ab2). Such Ab2 antibodies are produced by techniques well known to those skilled in the art. (See, e.g. Goding, J. W., *Monoclonal Antibodies: Principles and Practice,* 2ed., Academic Press (1986)). According to the subject invention, such Ab2 antibodies are mammalian in origin, usually murine, preferred human and, in order to reduce potential immunoginicity in humans, murine antibody may be humanized or chimerized by techniques well known to those skilled in the art. But one example of such an anti-idiotypic monoclonal antibody is the colorectal cancer associated anti-idiotypic monoclonal antibody 105AD7 described by Austin et al., *Immunology.* ( 1989)67:525–30.

In still another embodiment of the present invention, desired TAAs are produced by purification from a source unrelated to the tumor.

In yet another embodiment, the antigen is synthesized as described by Livingston et al., *J. Immunol.* (1987) 138:1524–29.

According to the present invention, liposomal formulations of highly purified TAAs may include immune system adjuvants, including one or more of LPS, lipid A, and muramyldipeptide (MDP) as described in *Liposomes,* Ostro, M. J., ed., Marcel Dekker, Inc., (1983) p. 249, or glucan, or certain cytokines including IL1, IL2, and gamma interferon.

Prior to administration to humans, the subject compounds are tested for safety and efficacy in a murine model bearing tumors transfected with TAA genes or the like.

The compounds of the subject invention are administered as anti tumor vaccines to patients either having cancer or at risk for the development of cancer. The compositions are formulated for parenteral administration, or alternatively for aerosol administration, by techniques well known to those skilled in the art. Following formulation, the compounds are administered in doses ranging from 0.01 µg to 100 mg, usually 0.1 µg to 10 mg, more usually 10 µg to 1 mg per dose in a volume of 0.1 to 5 ml for parenteral administration. Multiple doses may be administered as frequently as once a week for the first year, with booster innoculations occuring every 6 months to 5 years following initial vaccination.

According to the present invention, the antitumor vaccine compounds may be employed in cocktails of two or more different TAAs encapsulated in and/or conjugated to liposomes. Such cocktails may be of particular in certain highly metastatic cancers.

The following examples are offered by way of illustration and not limitation.

EXPERIMENTAL

EXAMPLE I

Disterolphosphatidylcholine, cholesterol, and dicetyl phosphate and methanol are used in a volumetric ratio of 5:1 in lipid solvents. Multilamellar liposomes (MLV) are prepared by the method described by Bangham, et al., with some modifications. Disterolphosphatidylcholine (70 mol %), cholesterol (24 mol %), and dicetyl phosphate (6 mol %) are mixed in a round bottomed flask and the lipid solvents are evaporated to dryness under a stream of nitrogen. The aqueous phase, containing GA733-2 in PBS, is added to the thin film of dried lipids in a flask at 42° C. (Lipophilic proteins may be subjected to detergent dialysis techniques well known to those skilled in the art as part of the encapsulation technique.) After 30 minutes of swelling time, the dispersion is completed at 42° C. by adding a few glass beads and vortexing the mixture vigorously for 15 minutes. The MLV liposomes thus formed are equilibrated for 2 hours at room temperature, purified, and used immediately.

The MLV liposomes are sized by a laser light sorter. Liposome preparations are passed through a Sephadex G-75 column to separate liposome-incorporated antigens from free proteins. Liposomes are eluted with void volume followed by unencapsulated protein. To estimate the efficacy of protein encapsulation in the vesicles, membrane antigens are labeled with $^{125}I$ iodobeads. Free $^{125}I$ is removed by extensive dialysis. The $^{125}I$-labeled proteins are used in the aqueous phase of MLV preparation described above and are passed through a Sephadex G-75 column. The percentage of radioactivity eluting with liposomes is taken as an index of encapsulation efficiency. Liposome compositions for use in mammalian hosts are prepared without radiolabeling. Under these conditions, the protein concentration is determined by protein assay as known to those of skill in the art. The GA733-2-liposome encapsulated compositions are stored at 4° C. under argon until formulation for administration into a mammalian host.

EXAMPLE II

Liposomes are prepared with phosphatidylcholine, cholesterol, and dicetylphosphate used in a molar ratio of 7:2:1. The lipids in chloroform:methanol (95:5) am brought to dryness in a round bottom flask by rotary evaporation under argon. The dried film of lipids are resuspended in 2 ml of 0.15M borate saline buffer at pH 8 containing 150 mg of GA733-2 TAA trace labeled with $^{125}I$. The suspension is allowed to incubate for 1 hour, sonicated in a bath type sonicator for 1 hour, and then left for a third hour before being loaded onto a lipid presaturated Sephadex G-200 column to remove the non-liposome-associated protein. The TAA content of the liposome peak is determined by the specific activity of the $^{125}I$ protein. Liposome compositions for use in mammalian hosts are prepared without radiolabeling and the protein concentration determined as previously described. The GA733-2-liposome encapsulated compositions are stored at 4° C. under argon until formulation for administration into a mammalian host.

EXAMPLE III

One mg of GA733-2, 75 mg of POPC (1-palmitoyl-2oleoyl-phosphatidylcholoine), and 175 ng of DOPG (1,2-dioleoyl phosphatidyl glycerol) in a total volume of 2.5 ml of tert-butanol are aliquoted into a 5 ml non-pyogenic vials, frozen at 4° C., and lyophilized over a period of 16 hours. The final preparations are stored at 4° C. under argon and remain stable for several months. For injection, the liposomes are reconstituted in 2.5 ml of sterile saline, added to the vial and allowed to sit for 15 seconds at room temperature. The vial is then vortexed for 30 seconds. This procedure results in liposomes in the size range of 0.1 to 3 µm.

EXAMPLE IV

Disterolphosphatidylcholine, cholesterol, and dicetyl phosphate and methanol are used in a volumetric ratio of 5:1 in lipid solvents. Multilamellar liposomes (MLV) are prepared by the method described by Bangham, et al., with some modifications. Disterolphosphatidylcholine (70 mol %), cholesterol (24 mol %), and dicetyl phosphate (6 mol %) are mixed in a round bottomed flask and the lipid solvents are evaporated to dryness under a stream of nitrogen. The aqueous phase, containing CO-029 in PBS, is added to the thin film of dried lipids in a flask at 42° C. (Lipophilic proteins may be subjected to detergent dialysis techniques well known to those skilled in the an as part of the encapsulation technique.) After 30 minutes of swelling time, the dispersion is completed at 42° C. by adding a few glass beads and vortexing the mixture vigorously for 15 minutes. The MLV liposomes thus formed are equilibrated for 2 hours at room temperature, purified, and used immediately.

The MLV liposomes are sized by a laser light sorter. Liposome preparations are passed through a Sephadex G-75 column to separate liposome-incorporated antigens from free proteins. Liposomes are eluted with void volume followed by unencapsulated protein. To estimate the efficacy of protein encapsulation in the vesicles, membrane antigens are labeled with $^{125}I$ iodobeads. Free $^{125}I$ is removed by extensive dialysis. The $^{125}I$-labeled proteins are used in the aqueous phase of MLV preparation described above and are passed through a Sephadex G-75 column. The percentage of radioactivity eluting with liposomes is taken as an index of encapsulation efficiency. Liposome compositions for use in mammalian hosts are prepared without radiolabeling. Under these conditions, the protein concentration is determined by protein assay as known to those of skill in the art. The CO-029-liposome encapsulated compositions are stored at 4° C. under argon until formulation for administration into a mammalian host.

EXAMPLE V

Liposomes are prepared with phosphatidylcholine, cholesterol, and dicetylphosphate used in a molar ratio of 7:2:1. The lipids in chloroform:methanol (95:5) are brought to dryness in a round bottom flask by rotary evaporation under argon. The dried film of lipids are resuspended in 2 ml of 0.15M borate saline buffer at pH 8 containing 150 mg of CO-029 TAA trace labeled with $^{125}I$. The suspension is allowed to incubate for 1 hour, sonicated in a bath type sonicator for 1 hour, and then left for a third hour before being loaded onto a lipid presaturated Sephadex G-200 column to remove the non-liposome-associated protein. The TAA content of the liposome peak is determined by the specific activity of the $^{125}I$ protein. Liposome compositions for use in mammalian hosts are prepared without radiolabeling and the protein concentration determined as previously described. The CO-029-liposome encapsulated compositions are stored at 4° C. under argon until formulation for administration into a mammalian host.

Liposomes are prepared with phosphatidylcholine, cholesterol, and dicetylphosphate used in a molar ratio of 7:2:1. The lipids in chloroform:methanol (95:5) are brought to dryness in a round bottom flask by rotary evaporation under argon. The dried film of lipids are resuspended in 2 ml of 0.15M borate saline buffer at pH 8 containing 150 mg of CO-029 TAA trace labeled with $^{125}$I. The suspension is allowed to incubate for 1 hour, sonicated in a bath type sonicator for 1 hour, and then left for a third hour before being loaded onto a lipid presaturated Sephadex G-200 column to remove the non-liposome-associated protein. The TAA content of the liposome peak is determined by the specific activity of the $^{125}$I protein. Liposome compositions for use in mammalian hosts are prepared without radiolabeling and the protein concentration determined as previously described. The CO-029-liposome encapsulated compositions are stored at 4° C. under argon until formulation for administration into a mammalian host.

EXAMPLE VI

One mg of CO-029, 75 mg of POPC (1-palmitoyl-2oleoyl-phosphatidylcholoine), and 175 ng of DOPG (1,2-dioleoyl phosphatidyl glycerol) in a total volume of 2.5 ml of tert-butanol are aliquoted into a 5 ml non-pyogenic vials, frozen at 4° C., and lyophilized over a period of 16 hours. The final preparations are stored at 4° C. under argon and remain stable for several months. For injection, the liposomes are reconstituted in 2.5 ml of sterile saline, added to the vial and allowed to sit for 15 seconds at room temperature. The vial is then vortexed for 30 seconds. This procedure results in liposomes in the size range of 0.1 to 3 µm.

EXAMPLE VII

The TAA GA-733-2 is conjugated to the surface of liposomes according to techniques described by Heath, T. D., supra. Essentially, saturated synthetic phosphatidylethanolamine conjugation lipid is activated by drying down 100 micromole of the lipid in a suitable reaction vessel. Lipid is redissolved in 10 ml of dry chloroform. 300 micromoles of triethylamine is added followed by 150 micromole of N-succinimidylpyridyldithiopropionate in 5 ml methanol. The mixture is stirred at room temperature under argon. The progress of the reaction is checked by thin layer chromatography using silica gel plates run in chloroform(65):methanol(25):water(4). The derivative gives a faster running spot than phosphatidylethanolamine and the spots are visualized with a phosphomolybdate spray. The reaction is complete when no more phosphatidylethanolamine is detected on the plates, generally 1 to 2 hours after initiation. The mixture is dried down, resuspended in chloroform, and applied to a 10 gram silicic acid column equilibrated with chloroform. The column is washed with 20 ml of chloroform and eluted with 20 ml portions of chloroform:methanol, first at 95:5, then at 90:10, then at 85:15, and finally at 80:20. Five ml fractions are collected and the pure derivative located by thin layer chromatography. The fractions are pooled, concentrated by evaporation at reduced pressure in a rotary evaporator, and rechecked for purity by thin layer chromatography. The product is stored at −20° C. under argon in chloroform solution in sealed ampules.

GA-733-2 is thiolated with N-succinimidylpyridyldithiopropionate. A solution of aggregate-free GA-733-2 is prepared in 0.1M sodium phosphate and 0.1M sodium chloride, at pH 7.5. The GA-733-2 concentration is about 2–6 mg/ml. N-succinimidylpyridyldithiopropionate solution is prepared in ethanol at 20 micromole/ml. N-succinimidylpyridyldithiopropionate is then added dropwise to the GA-733-2 solution to give a molar ratio of 15:1 N-succinimidylpyridyldithiopropionate:GA-733-2, wherein the ethanol concentration does not exceed 1%. The mixture is allowed to react at room temperature for 30 minutes. The product is separated from the reactants by gel chromatography on Sephadex G-50 equilibrated with 0.05M sodium citrate, 0.05M sodium phosphate, 0.05M sodium chloride, pH 7.0. The thiolated GA-733-2 is characterized by measuring the number of pyridylthiols per molecule as described by Carlsson et al., Biochem. J. ( 1978)173:723. The pyridyldithio-GA-733-2 product is stored at 4° C. following sterilization by filtration.

Just prior to conjugation, the pyridyldithio-GA-733-2 is reduced to generate thiols by placing the product in citrate phosphate buffer pH 7.0 and titrating to pH 4.5 by the addition of small mounts of 1N HCl. A 2.5M solution of dithiothreitol is prepared in 0.1M acetate buffer pH 4.5, and 10 µl of this solution are added to each ml of the protein solution. After 30 minutes the protein solution is separated from the dithiothreitol by gel chromatography on a Sephadex G-75 column equilibrated with pH 6.7 buffer purged with nitrogen or argon to remove dissolved oxygen. The protein fractions are collected under inert gas to exclude oxygen.

Liposomes are prepared by any known technique, for example from phosphatidylcholine and cholesterol in 1:1 or 2:1 molar ratio. The conjugation lipid is added to the other lipids at a concentration of 1–5 mole per 100 mole of lipid.

Thiolated GA-733-2 is conjugated to the liposomes by mixing at pH 6.0–8.0 and the reaction allowed to proceed overnight. Unreacted thiols are blocked with Ellman's reagent and liposomes separated from non-conjugated protein by gel chromatography or centrifugation, preferably by centrifugation to avoid loss of liposomes on the gel matrices. The conjugate compositions are stored at 4020 C. under until formulation for administration into a mammalian host.

EXAMPLE VIII

The TAA CO-029 is conjugated to the surface of liposomes according to techniques described by Heath, T. D., supra. Essentially, saturated synthetic phosphatidylethanolamine conjugation lipid is activated by drying down 100 micromole of the lipid in a suitable reaction vessel. Lipid is redissolved in 10 ml of dry chloroform. 300 micromoles of triethylamine is added followed by 150 micromole of N-succinimidylpyridyldithiopropionate in 5 ml methanol. The mixture is stirred at room temperature under argon. The progress of the reaction is checked by thin layer chromatography using silica gel plates run in chloroform(65):methanol(25):water(4). The derivative gives a faster running spot than phosphatidylethanolamine and the spots are visualized with a phosphomolybdate spray. The reaction is complete when no more phosphatidylethanolamine is detected on the plates, generally 1 to 2 hours after initiation. The mixture is dried down, resuspended in chloroform, and applied to a 10 gram silicic acid column equilibrated with chloroform. The column is washed with 20 ml of chloroform and eluted with 20 ml portions of chloroform:methanol, first at 95:5, then at 90:10, then at 85:15, and finally at 80:20. Five ml fractions are collected and the pure derivative located by thin layer chromatography. The fractions are pooled, concentrated by evaporation at reduced pressure in a rotary evaporator, and rechecked for purity by thin layer chromatography. The product is stored at −20° C. under argon in chloroform solution in sealed ampules.

CO-029 is thiolated with N-succinimidylpyridyldithiopropionate. A solution of aggregate-free CO-029 is prepared in 0.1M sodium phosphate and 0.1M sodium chloride, at pH 7.5. The CO-029 concentration is about 2-6 mg/ml. N-succinimidylpyridyldithiopropionate solution is prepared in ethanol at 20 micromole/ml. N-succinimidylpyridyldithiopropionate is then added dropwise to the CO-029 solution to give a molar ratio of 15:1 N-succinimidylpyridyldithiopropionate:CO-029, wherein the ethanol concentration does not exceed 1%. The mixture is allowed to react at room temperature for 30 minutes. The product is separated from the reactants by gel chromatography on Sephadex G-50 equilibrated with 0.05M sodium citrate, 0.05M sodium phosphate, 0.05M sodium chloride, pH 7.0. The thiolated CO-029 is characterized by measuring the number of pyridylthiols per molecule as described by Carlsson et al., *Biochem. J.* (1978)173:723. The pyridyldithio-CO-029 product is stored at 4° C. following sterilization by filtration.

Just prior to conjugation, the pyridyldithio-CO-029 is reduced to generate thiols by placing the product in citrate phosphate buffer pH 7.0 and titrating to pH 4.5 by the addition of small amounts of 1N HCl. A 2.5M solution of dithiothreitol is prepared in 0.1M acetate buffer pH 4.5, and 10 µl of this solution are added to each ml of the protein solution. After 30 minutes the protein solution is separated from the dithiothreitol by gel chromatography on a Sephadex G-75 column equilibrated with pH 6.7 buffer purged with nitrogen or argon to remove dissolved oxygen. The protein fractions are collected under inert gas to exclude oxygen.

Liposomes are prepared by any known technique, for example from phosphatidylcholine and cholesterol in 1:1 or 2:1 molar ratio. The conjugation lipid is added to the other lipids at a concentration of 1–5 mole per 100 mole of lipid.

Thiolated CO-029 is conjugated to the liposomes by mixing at pH 6.0–8.0 and the reaction allowed to proceed overnight. Unreacted thiols are blocked with Ellman's reagent and liposomes separated from non-conjugated protein by gel chromatography or centrifugation, preferably by centrifugation to avoid loss of liposomes on the gel matrices. The conjugate compositions are stored at 4° C. under until formulation for administration into a mammalian host.

EXAMPLE IX

Anti-idiotypic or Ab2 monoclonal antibodies (MAb) mimicking either GA733-2 or CO-029 tumor associated antigens are produced by techniques known to those skilled in the art. (See, e.g. Coding, J. W., *Monoclonal Antibodies: Principles and Practice.* 2ed., Academic Press (1986)). Essentially, either protein, or the tumor cell line from which the protein is derived, is employed as an immunogen to produce anti-antigen monoclonal antibody or Ab1 in a mammalian host, usually murine, and, most frequently, Balb C mice. The protein or cell line may be injected with or without an adjuvant such as complete or incomplete Freund's adjuvant or the like. Monoclonal antibody (Ab1) is then employed as an immunogen to produce Ab2 anti-idiotypic monoclonal antibodies by similar methods. Alternatively, existing MAb to either antigen may be employed as immunogen to produce Ab2 such as MAb GA733 reported by Herlyn, et al., *Science* (1986) 232:100–02.

Anti-TAA Ab2 antibodies are encapsulated into liposomes by techniques well known to those skilled in the art. Alternatively, such immunoglobulin molecules may be conjugated to the surface of liposomes as described above.

EXAMPLE X

Normal mice display the murine analog of GA733-2 and CO-029 (>80% homology) in a tissue distribution similar to the distribution of the antigen in humans. In addition, a murine tumor, e.g. P815 or CT3, is transfected by techniques well known to those skilled in the art with the cDNA encoding the human GA733-2 and CO-029 antigens resulting in the stable expression of the human gene products on the surface of the murine tumors. The tumors are subsequently introduced into normal mice and proliferate while continuing to express the recombinant antigens. This model allows testing of both safety and efficacy of the subject liposomal vaccines.

For safety testing, either normal or tumor bearing mice are vaccinated with various formulations of either GA733-2, CO-029 or anti-idiotypic monoclonal antibodies in any of the subject liposomal compositions in doses ranging from 0.01 µg to 100 mg, usually 0.1 µg to 10 µg, more usually 10 µg to 1 mg total antigen per dose up to six doses. Vaccination is administered i.p., i.m., s.c., or via foot pad in volumes of 10 µl to 2 ml. Results are assessed by serial determinations of weight, clinical observations, laboratory parameters including complete blood counts, chemistries, and gross histopathology at necropsy.

For efficacy testing, mice are subjected to the same immunization regimen prior to, during, or post tumor implantation. Efficacy is measured by 1) determinations of tumor growth following subcutaneous implantations, 2) enumeration of tumor nodules in a micro-metastatic model and/or 3) gross survival. Efficacy is also measured by determination of immunological responses including but not limited to antigen specific antibody titer, delayed type hypersensitivity, ADCC, and cytotoxic T lymphocytes.

EXAMPLE XI

Patients with cancer may have the cancer surgically excised and then be given the subject tumor vaccines. If clinical, laboratory, and radiologic examination reveals no evidence of gross disease, the treatment is considered to be "surgical adjuvant treatment." Vaccinations can also be commenced prior to surgery, in which case it is considered "neoadjuvant therapy." Patients with cancer who develop metastatic disease which is not surgically resected can also be treated.

Patients are vaccinated with various formulations of either GA733-2, CO-029, or anti-idiotypic monoclonal antibodies in any of the subject compositions. The route may be intramuscular (i.m.), subcutaneous (s.q.), or intradermal (i.d.). The dose of antigen administered is 0.01 µg to 100 mg, usually 0.1 µg to 10 mg, more usually 10 µg to 1 mg per dose in a volume of 0.1 to 5 ml for parenteral administration. The vaccine is administered as often as weekly for the first 6 months and as infrequently as monthly, bimonthly, or every 3 or 6 months for the first year. A booster may be given in subsequent years at intervals of 1–12 months.

An alternate approach is to administer the initial immunization with a live recombinant carrier expressing the relevant antigen with the subsequent boost consisting of liposomes carrying the relevant purified antigen given according to the schedules described above.

EXAMPLE XII

Normal human subjects or subjects who are at high risk for the development of certain malignancies are vaccinated according to the schedule described above with subsequent boosters once every 6 months to 5 years. Examples of patients at high risk for the development of malignancy include those with familial polypoposis for colorectal cancer or those who smoke for lung cancer.

It will be apparent to those of skill in the art that the present invention adds to the state of the art liposomal formulations of highly purified minor associated antigens useful in the treatment and prevention of a variety of cancers.

Although the present invention has been described in some detail for the purposes of clarity and understanding, it will be obvious to those skilled in the art that certain changes and modifications may be practiced within the scope of the appended claims.

What is claimed is:

1. An antitumor vaccine composition comprising, as active ingredient, a GA733-2 antigen, said antigen being encapsulated in, or covalently bound to, a liposome carrier.

2. The vaccine composition of claim 1 which further contains an additional synthetically prepared tumor associated antigen.

3. An antitumor vaccine composition comprising, as an active ingredient, an anti-idiotypic antibody that immunologically mimics the GA733-2 antigen encapsulated in, or covalently bound to, a liposome carrier.

4. A method for treating tumors that express the GA733-2 antigen comprising the step of administering an antitumor vaccine composition comprising, as active ingredient, a GA733-2 antigen, said antigen being encapsulated in, or covalently bound to, a liposome carrier.

5. The method of claim 4 wherein said vaccine further contains an additional synthetically prepared tumor associated antigen.

6. A method for treating tumors that express the GA733-2 antigen comprising the step of administering an antitumor vaccine composition comprising, as an active ingredient, an anti-idiotypic antibody that immunologically mimics the GA733-2 antigen encapsulated in, or covalently bound to, a liposome carrier.

* * * * *